United States Patent [19]

Schor et al.

[11] 4,389,393

[45] Jun. 21, 1983

[54] SUSTAINED RELEASE THERAPEUTIC COMPOSITIONS BASED ON HIGH MOLECULAR WEIGHT HYDROXYPROPYLMETHYLCELLULOSE

[75] Inventors: Joseph M. Schor, Locust Valley; Ashok Nigalaye, Jackson Heights, both of N.Y.; Norman G. Gaylord, New Providence, N.J.

[73] Assignee: Forest Laboratories, Inc., New York, N.Y.

[21] Appl. No.: 362,104

[22] Filed: Mar. 26, 1982

[51] Int. Cl.³ .......................... A61K 9/22; A61K 9/26
[52] U.S. Cl. ........................................ 424/19; 424/22; 424/35; 424/362
[58] Field of Search ..................... 424/19–22, 424/35, 362

[56] References Cited

U.S. PATENT DOCUMENTS

| | | | |
|---|---|---|---|
| 2,887,440 | 5/1959 | Greminger et al. | 424/362 |
| 3,065,143 | 11/1962 | Christenson et al. | 424/19 |
| 3,839,319 | 10/1974 | Greminger et al. | 424/362 |
| 3,852,421 | 12/1974 | Koyanagi et al. | 424/362 |
| 3,870,790 | 3/1975 | Lowey et al. | 424/19 |
| 4,091,205 | 5/1978 | Onda et al. | 424/362 |
| 4,167,558 | 9/1979 | Sheth et al. | 424/19 |
| 4,226,849 | 10/1980 | Schor | 424/19 |
| 4,259,314 | 3/1981 | Lowey | 424/19 |
| 4,265,875 | 5/1981 | Byrne et al. | 424/362 |
| 4,292,299 | 9/1981 | Suzuki et al. | 424/19 |

*Primary Examiner*—Shep K. Rose
*Attorney, Agent, or Firm*—Jacobs & Jacobs

[57] ABSTRACT

A carrier base material combined with a therapeutically active medicament and shaped and compressed to a solid unit dosage form having a regular and prolonged release pattern upon administration, the carrier base material being one or more hydroxypropylmethylcelluloses or a mixture of one or more hydroxypropylmethylcelluloses and up to 30% by weight of the mixture of methylcellulose, sodium carboxymethylcellulose and/or other cellulose ether, and wherein at least one of the hydroxypropylmethylcelluloses has a methoxy content of 16-24 weight-%, a hydroxypropoxyl content of 4-32 weight-% and a number average molecular weight of at least 50,000 and wherein the carrier base material constitutes less than about one third of the weight of the solid unit dosage form.

10 Claims, No Drawings

SUSTAINED RELEASE THERAPEUTIC COMPOSITIONS BASED ON HIGH MOLECULAR WEIGHT HYDROXYPROPYLMETHYLCELLULOSE

BACKGROUND OF THE INVENTION

1. Field of Invention

This invention relates to a carrier base material to be combined with a therapeutically active medicament and formed into a solid, shaped dosage unit having a long-lasting and regular incremental release of the medicament upon administration. Specifically, this invention relates to a carrier base material, consisting essentially or predominantly of hydroxypropylmethylcellulose having a chemical structure and molecular weight which renders it suitable for use, in relatively low concentrations, in sustained release therapeutic compositions.

2. Description of the Prior Art

Hydroxypropylmethylcelluloses are commercially available in various grades, under several tradenames, including Methocel E, F, J and K (all previously designated as Methocel HG) from The Dow Chemical Co., U.S.A., HPM from British Celanese Ltd., England, and Metalose SH from Shin-Etsu, Ltd., Japan. The various grades available under a given tradename represent differences in methoxyl and hydroxypropoxyl content as well as molecular weight. The methoxyl content ranges from 16.5 to 30 weight-% and the hydroxypropoxyl content ranges from 4 to 32 weight-%, as determined by the method described in ASTM D-2363-72.

Commercial designations of the various hydroxypropylmethylcelluloses are based on the viscosities of 2% aqueous solutions at 20° C. The viscosities range from 15 cps to 30,000 cps and represent number average molecular weights ranging from about 10,000 to over 150,000, as calculated from the data in "Handbook of Methocel Cellulose Ether Products" (The Dow Chemical Co., 1974).

A solid unit dosage form consisting of a mixture of a medicament and a carrier base material which is low molecular weight hydroxypropylmethylcellulose Methocel E50, formerly known as Methocel 60HG 50 cps, having a number average molecular weight of 23,000, a methoxyl content of 28-30 weight-% and a hydroxypropoxyl content of less than 9 weight-%, rapidly releases the medicament when brought into contact with the aqueous fluids of the mouth or the gastrointestinal tract. However, an effective "sustained release" tablet is produced by admixture of a medicament with a modified Methocel E50, per se or in admixture with other cellulose ethers. As disclosed by Lowey and Stafford (U.S. Pat. No. 3,870,790) and Schor (U.S. Pat. No. 4,226,849), the modification is carried out by exposure of the low molecular weight hydroxypropylmethylcellulose Methocel E50 to high humidity or moisture and drying in air.

In our co-pending application, Ser. No. 332,348 filed 12/18/81 it was disclosed that effective prolonged release therapeutic compositions may be prepared by using as a carrier base material a hydroxypropylmethylcellulose having a hydroxypropoxyl content of 9-12 weight-% and a number average molecular weight of less than 50,000, e.g. Metalose 60SH50. The carrier base material provides sustained release characteristics without treatment or modification.

Christenson and Huber (U.S. Pat. No. 3,590,117) reported that high viscosity grade, i.e. 15,000 cps, hydroxypropylmethylcellulose did not make an acceptable long-lasting troche because the troche would flake off in the mouth rather than dissolve uniformly.

Christenson and Dale (U.S. Pat. No. 3,065,143) disclosed the use of certain high molecular weight hydrophilic gums, including hydroxypropylmethylcelluloses, in the preparation of a "sustained release tablet". The tablet consisted essentially of a mixture of a medicament and at least one third part by weight of the weight of the tablet of a hydrophilic gum which rapidly absorbed water and swelled at 37° C. to form a "soft mucilaginous gel barrier" on the surface of the tablet when brought into contact with the aqueous fluids of the gastrointestinal tract.

The high molecular weight hydroxypropylmethylcelluloses disclosed by Christenson and Dale and constituting at least one third of the weight of the tablet, include Methocel 60HG 4000 cps, now known as Methocel E4M, having a 28-30 weight-% methoxyl content, a 7.5-12 weight-% hydroxypropoxyl content and a number average molecular weight of 93,000, and Methocel 90HG 4000 cps and Methocel 90HG 15,000 cps, now known as Methocel K4M and Methocel K15M, respectively. The latter have number average molecular weights of 89,000 and 124,000, respectively, and a 19-24 weight-% methoxyl content, and a 4-12 weight-% hydroxypropoxyl content.

The present invention is directed toward further improvements in carrier base materials containing hydroxypropylmethylcelluloses for use in the preparation of sustained release solid pharmaceutical unit dosage forms, particularly with moisture sensitive and/or high dosage medicaments.

SUMMARY OF THE INVENTION

An object of the present invention is to provide a carrier material for use in the preparation of orally, bucally or sublingually, etc., administered lozenges and tablets, as well as suppositories and other solid unit dosage forms which have a regular and sustained release pattern for a systemically absorbable medicament or active ingredient incorporated therein.

Another object of the present invention is to provide a carrier base having greater stability, greater hardness, lower friability, reduced water solubility and a uniform sustained release pattern from hydroxypropylmethylcellulose, particularly for use with moisture sensitive medicaments.

A further object of the present invention is to provide a carrier base which comprises less than about 30 weight-% of the weight of the solid unit dosage form, permitting the preparation of smaller units which are easier to administer.

Still another object of the present invention is to provide a carrier base for use with high dosage medicaments in sustained release dosage forms.

It has now been found that these improvements in a carrier base can be achieved by utilizing a high viscosity grade hydroxypropylmethylcellulose having a number average molecular weight above 50,000 and a methoxyl content of 16-24 weight-%, wherein said carrier base constitutes less than about one third of the weight of the sustained release dosage form.

DETAILED DESCRIPTION OF THE INVENTION

According to the present invention, it has now been found that important advantages and improvements over prior products containing hydroxypropylmethylcelluloses, as described in U.S. Pat. Nos. 3,065,143, 3,870,790 and 4,226,849, can be obtained by utilizing a high viscosity grade hydroxypropylmethylcellulose having a methoxyl content of 16-24 weight-%. The hydroxypropylmethylcellulose used in the present invention has a number average molecular weight above 50,000 and a hydroxypropoxyl content of 4-32 weight-%.

The hydroxypropylmethylcelluloses which are effective in the present invention include, but are not limited to, commercially available 4000 and 15,000 cps viscosity grades of Methocel K, i.e. Methocel K4M and Methocel K15M, available from the Dow Chemical Co., U.S.A., and 4000, 15,000 and 39,000 cps viscosity grades of Metalose 90SH, available from Shin-Etsu Ltd., Japan, as well as 5,000, 12,000 and 75,000 cps viscosity grades of Methocel J, i.e. Methocel J5M, J12M, J20M and J75M, available from the Dow Chemical Co.

Although U.S. Pat. No. 3,065,143 disclosed that a sustained release tablet required the presence of at least one third of the weight of the tablet of these hydroxypropylmethylcelluloses, it has surprisingly been found that effective sustained release can be obtained from solid dosage forms containing as little as 5 to about 30 weight-% of these hydroxypropylmethylcelluloses.

Numerous advantages result from the ability to use less than about 30% of the carrier base material in a sustained release dosage form. These include the use of smaller tablets which are more economical and are easy to administer. High dosage drugs which normally result in large tablets can be put in smaller sustained-release dosage form.

Cellulose ethers such as the hydroxypropylmethylcelluloses of the present invention are hydrophilic and tend to absorb moisture from the atmosphere. The use of low levels of the cellulose ether in a solid dosage form results in a lower moisture content upon exposure to the atmosphere. This is particularly important when the active medicament is moisture sensitive and undergoes decomposition and/or hydrolysis upon contact with moisture. Typical moisture sensitive drugs include aspirin, phenacetin, procainamide, nikethamide, polymixin, barbiturates, idoxuridine, hydantoins, angiotensinamide, nitroglycerin, benzocaine, scopolamine, meperidine, codeine, streptomycin, ascorbic acid, sulfonamide drugs, tolbutamide, antihistamine salts such as chlorpheniramine and brompheniramine, phenylephrine, diphenhydramine, diethylcarbamazine, theophylline, caffeine, alkaloid salts, adrenocortical steroid esters such as hydrocortisone phosphate, and the like.

The hydroxypropylmethylcelluloses of the present invention may be used without prior humidification or similar treatment and when mixed with an active medicament, the mixture has excellent compressibility and the tablets prepared therefrom are hard and dense, have low friability and provide sustained release over an extended period. Treatment of the carrier base material by humidification and drying before incorporation in a sustained release tablet has little or no effect on the compressibility of the polymer and the properties of the tablets prepared therefrom.

Sustained release drug forms containing the hydroxypropylmethylcelluloses of the present invention are stable and the release rate does not change over an extended storage period. The therapeutic compositions of the present invention, in most cases, give a steady, reproducible release of the active medicament.

A hydroxypropylmethylcellulose having a methoxyl content of 16-24 weight-% and a number average molecular weight above 50,000 can be used as the sole carrier base material or can be used in admixture in all proportions with other hydroxypropylmethylcelluloses of the same structure with a higher or a lower but above 50,000 number average molecular weight, e.g. a 30/70 or 70/30 mixture of Methocel K4M and Methocel K15M. A hydroxypropylmethylcellulose having a different structure and a number average molecular weight above 50,000 can also be used in admixture with the high molecular weight hydroxypropylmethylcellulose having a methoxyl content of 16-24 weight-%, e.g. a 30/70 or 50/50 mixture of Methocel E4M and Methocel K4M.

The hydroxypropylmethylcelluloses of the present invention can be optionally mixed with about 0 to 30% by weight of the mixture of a hydroxypropylmethylcellulose with the same or different structure and a number average molecular weight below 50,000, or methylcellulose, sodium carboxymethylcellulose or other cellulose ether.

The active ingredient can be of any type of medication which acts locally in the mouth or systemically, which in the case of the latter, can be administered orally to transmit the active medicament into the gastrointestinal tract and into the blood, fluids and tissues of the body without excessive peak concentrations occurring. Alternatively, the active ingredient can be of any type of medication which acts through the buccal tissues of the mouth to transmit the active ingredient directly into the blood stream thus avoiding first pass liver metabolism and by-passing the gastric and intestinal fluids which have an adverse inactivating or destructive action on many active ingredients unless they are especially protected against such fluids as by means of an enteric coating or the like. The active ingredient can also be of a type of medication which can be transmitted into the blood circulation through the rectal tissues.

Representative active medicaments include antacids, anti-inflammatory substances, coronary vasodilators, cerebral vasodilators, peripheral vasodilators, anti-infectives, psychotropics, antimanics, stimulants, antihistamines, laxatives, decongestants, vitamins, gastrointestinal sedatives, antidiarrheal preparations, antianginal drugs, vasodilators, antiarrythmics, anti-hypertensive drugs, vasoconstrictors and migraine treatments, anticoagulants and antithrombotic drugs, analgesics, anti-pyretics, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs, and other drugs or substances acting locally in the mouth, such as topical analgetics, local anaesthetics, etc.

The hydroxypropylmethylcelluloses of the present invention are particularly effective in the preparation of sustained release unit dosage forms containing moisture sensitive medicaments such as those named earlier. However, it is to be understood that the invention is applicable to sublingual lozenges, suppositories and compressed tablets, the latter intended to be swallowed in unit dosage form and which upon ingestion according to a prescribed regimen give slow and regular release of active medicament while being protected against normally inactivating gastric fluids.

The hydroxypropylmethylcellulose having a methoxyl content of 16-24 weight-%, a number average molecular weight of more than 50,000 and present in a concentration of less than about one-third of the total weight of the dosage form, forms what is called a long-acting, slow dissolving carrier of such a nature that it has a protective, demulcent and buffering effect in the body and causes the active medicament to exert its optimum therapeutic action immediately and incrementally for many hours, so that full therapeutic advantage can be taken of the entire or substantially the entire amount of active medicament administered. This unexpectedly high degree of efficiency is a particular advantage of the invention and minimizes the side effects of the medication.

In making up tablets containing an orally administrable systemically absorbable active component such as one of the heretofore mentioned medicaments, the oral carrier material is thoroughly intermixed with the medicament which is also in powdered or granular form or in solution, and any other needed ingredients which are conventional in tablet making such as magnesium stearate, lactose, starch and, in general, binders, fillers, disintegrating agents and the like. The complete mixture, in an amount sufficient to make a uniform batch of tablets, e.g. 50,000, of which each contains an effective amount of active medicament, is then subjected to tableting in conventional tableting machines at compression pressures of 2000 to 16000 lbs/sq.in. and, because of the use of the specific carrier material of this invention in the production of the tablets, a product is obtained which has the desired hardness, low level of friability and a predetermined prolonged action and a regular delayed release pattern so that the medicament is available over a period of 1 to 36 hours, depending on the precise tablet size, hardness and the particular carrier composition. In this way, it is possible to produce sustained or slow continuous release tablets in relatively simple and economical manner on a commercial scale as contrasted with the more elaborate and more complex materials and procedures heretofore employed or proposed.

The moisture content of the carrier used in the preparation of the sustained release tablets may be in the 0.1-10% range, the lower end of the range being preferable when moisture sensitive medicaments are used. If the moisture content is outside of this range, it may be brought within the range by the use of ambient or hot, dry or wet air, using appropriate equipment including static, convection, forced air or vacuum chambers or other equipment well known to those skilled in the art. The moisture content of the carrier during tableting influences the integrity of the tablet obtained under a given compression pressure. However, the moisture content has little or no influence on the sustained release characteristics and plays a minor role as compared to the chemical structure of the carrier and its concentration on the rate of release of medicaments. Similarly, while the release rate is governed at least in part by the size of the tablet or other shaped dosage form, as well as by the degree of compression, the chemical structure of the hydroxypropylmethylcellulose superimposes its effect and is the dominant factor in the control of the release rate.

The release pattern of active medicament from the carrier of the present invention can be controlled according to the particular medication and its intended therapeutic effect. For a sublingual lozenge or tablet, the release pattern may be varied from about 15 minutes to 4 hours. For orally administered tablets, the rate of release may be 2-4 hours, 4-8 hours, 8-10 hours, 10-12 hours, 15-18 hours, 20-24 hours, etc., as desired. For vaginal and rectal suppositories, the release pattern ranges from 2 to 36 hours, and can be less where indicated. Predetermined release patterns of unusually reliable and constant characteristics can be secured. This is often very important medically, especially when treating patients having coronary diseases, such as angina pectoris with nitroglycerin, or related problems of circulatory disorders or abnormal blood pressure conditions or psychotropic disorders such as manic depression or schizophrenia. The invention is particularly important also in treating such conditions as ulcerated tissue or mucous lesions and other conditions which arise from local hyperacidity or metabolic dysfunction in the physiological system. The invention is therefore of very versatile and adaptable nature giving it a wide range of application and end use.

The following illustrative embodiments of the disclosures of the present invention are non-limiting and variations will be obvious to those skilled in the art.

Examples 1-6 describe the preparation of controlled release 650 mg aspirin tablets.

EXAMPLES 1-2

Controlled release 650 mg aspirin tablets containing 13.2% Methocel K4M were prepared from untreated Methocel K4M having a moisture content of 2.5% and from treated Methocel K4M which had been exposed to 85% humidity for 24 hours and then dried in a forced air oven at 120° F. to a moisture content of 5.0%.

The 650 mg aspirin tablets were prepared from the following ingredients:

| | Ingredients | grams | mg/tablet |
|---|---|---|---|
| 1 | Aspirin (40 mesh) | 1300 | 650 |
| 2 | Methocel K4M | 200 | 100 |
| 3 | Hydrogenated vegetable oil (Lubritab) | 14 | 7 |
| 4 | Fumed silica (Cab-O-Sil M-5) | 1 | 0.5 |

Ingredients 1 and 2 were mixed, ingredient 3 was added to the blend and, after mixing, was followed by ingredient 4. The mixture was blended for 20 minutes and then subjected to compression in a tableting machine having a 0.281×0.625 inch punch, under a compression pressure of 4000 psi, to make 2000 capsule shaped tablets bisected on one side. The average weight of the tablets was 760 mg from untreated Methocel K4M and 750 mg from treated Methocel K4M. The thickness of the tablets was 0.264-0.280 inches from the former and 0.260-0.265 inches from the latter.

The hardness of the tablets was determined on a Pennwalt Stokes hardness tester. The friability was determined in a Erweka Friabilator (Erweka-Apparatebau GmbH, Heuenstamm Kr. Offenbach- /Main, West Germany) by measuring the weight loss after 3 minutes rotation.

The release rate was determined by using the release rate apparatus as described in NF XIV, page 985. Five tablets were placed into a 100 ml screw cap dissolution vial and 60 ml of a buffered solution of the desired pH, preheated to 37° C., was added to the vial. The vial was closed and rotated in the NF time release apparatus maintained at 40±2 rpm. At intervals of one hour, the vial was opened and the supernatant liquid was poured through a screen and collected. The collected liquid was quantitatively transferred to a 100 ml volumetric flask. The tablets on the screen and the vial were washed with deionized water, the washings being added to the flask. The washed tablets were returned to the vial from the screen with the aid of the next buffered solution and the closed vial was rotated in the bath for the next interval of one hour. The following schedule of buffered solutions was used:

| Hours | pH  | Hours | pH  |
|-------|-----|-------|-----|
| 1     | 1.2 | 9     | 7.5 |
| 2     | 2.5 | 10    | 7.5 |
| 3     | 4.5 | 11    | 7.5 |
| 4     | 4.5 | 12    | 7.5 |
| 5     | 7.0 | 13    | 7.5 |
| 6     | 7.0 | 14    | 7.5 |
| 7     | 7.5 | 15    | 7.5 |
| 8     | 7.5 | 16    | 7.5 |

The solutions separated from the tablets were analyzed for the concentration of medicament released from the tablets. The procedure was continued until at least 90% of the tablet has dissolved and/or essentially all of the medicament had been released.

The 650 mg aspirin tablets had the following properties:

|  | Example No. | | | |
|---|---|---|---|---|
|  | 1 | | 2 | |
| Methocel K4M | Untreated | | Treated | |
| Hardness, kg | 7.5–8.5 | | 9.0–10.0 | |
| Friability, % | 0.4 | | 0.26 | |
| Release rate | | Cumulative | | Cumulative |
| Hour | % | % | % | % |
| 1 | 8.9 | 8.9 | 10.8 | 10.8 |
| 2 | 11.6 | 20.5 | 10.8 | 21.6 |
| 3 | 10.6 | 31.1 | 12.0 | 33.6 |
| 4 | 10.2 | 41.3 | 10.7 | 44.3 |
| 5 | 12.4 | 53.7 | 13.5 | 57.8 |
| 6 | 8.3 | 62.0 | 10.7 | 68.5 |
| 7 | 13.6 | 75.6 | 9.4 | 77.9 |
| 8 | 7.5 | 83.1 | 5.5 | 83.4 |
| 9 | 3.8 | 86.9 | 4.3 | 87.7 |
| 10 | 3.0 | 89.9 | 3.3 | 91.0 |
| 13 | — | — | — | 98.1 |
| 14 | — | 100.9 | — | — |

Although the controlled release tablets prepared with treated and untreated Methocel K4M had comparable properties and release rates, the storage stability of the aspirin made with the treated carrier base material was about 18 months while that made with the untreated carrier base material was more than 3 years.

EXAMPLES 3–4

Controlled release 650 mg aspirin tablets containing 9.0% Methocel K4M were prepared from treated Methocel K4M which had been exposed to 85% humidity for 24 hours and then dried in a forced air oven at 120° F. to a moisture content of 5.0% and from treated Methocel K4M which was dried in an oven at 210° F. to a moisture content of 2.3%.

The 650 mg aspirin tablets were prepared from the following ingredients:

| | Ingredients | Treated Methocel grams | Treated Dried Methocel grams | mg/tablet |
|---|---|---|---|---|
| 1 | Aspirin (40 mesh) | 6500 | 650 | 650 |
| 2 | Methocel K4M | 650 | 65 | 65 |
| 3 | Lubritab | 70 | 7 | 7 |
| 4 | Cab-O-Sil M-5 | 5 | 0.5 | 0.5 |

The ingredients were mixed in the same manner as in Examples 1–2. The mixture was subjected to compression in a tableting machine having a 0.281×0.625 inch punch under a compression pressure of 4000 psi to make 10,000 capsule shaped tablets bisected on one side from the treated Methocel K4M and 1000 capsule shaped tablets from the treated and dried Methocel K4M.

The tablets from the treated Methocel K4M an average weight of 724 mg and a thickness of 0.250–0.260 inches while the tablets from the treated an dried Methocel K4M had an average weight of 714 mg and a thickness of 0.250–0.260 inches.

The hardness, friability and release rate of the 650 mg aspirin tablets were determined as described earlier to give the following results:

| | Example No. | | | |
|---|---|---|---|---|
|  | 3 | | 4 | |
| Methocel K4M | Treated | | Treated-Dried | |
| Hardness, kg | 8.0–10.0 | | 7.0–8.0 | |
| Friability, % | 0.2 | | 0.48 | |
| Release rate | | Cumulative | | Cumulative |
| Hour | % | % | % | % |
| 1 | 12.5 | 12.5 | 10.7 | 10.7 |
| 2 | 12.5 | 25.0 | 12.1 | 22.8 |
| 3 | 12.5 | 37.5 | 14.4 | 37.2 |
| 4 | 12.5 | 50.0 | 13.2 | 50.4 |
| 5 | 15.4 | 65.4 | 16.7 | 67.1 |
| 6 | 10.5 | 75.9 | 12.8 | 79.9 |
| 7 | 11.0 | 86.9 | 11.6 | 91.5 |
| 8 | 5.4 | 92.3 | 4.9 | 96.4 |
| 9 | 2.8 | 95.1 | 3.1 | 99.5 |

EXAMPLE 5

Controlled release 650 mg aspirin tablets containing 2.7% Methocel E4M and 6.3% Methocel K4M were prepared from untreated hydroxypropylmethylcelluloses with moisture contents in the range of 2–3%.

The 650 mg aspirin tablets were prepared from the following ingredients:

| | Ingredients | grams | mg/tablets |
|---|---|---|---|
| 1 | Aspirin | 650 | 650 |
| 2 | Methocel E4M | 19.5 | 19.5 |
| 3 | Methocel K4M | 45.5 | 45.5 |
| 4 | Lubritab | 7 | 7 |
| 5 | Cab-O-Sil M-5 | 0.5 | 0.5 |

Ingredient 1 was placed in a bag. Ingredients 2 and 3 were added and mixed with ingredient 1. Ingredients 4 and 5 were mixed with the blend of ingredients 1, 2 and 3 for 20 minutes. The mixture was subjected to compression in a tableting machine having a 0.281×0.625 inch punch under a compression pressure of 5000 psi to make 1000 capsule shaped tablets bisected on one side.

The average weight of the tablets was 717 mg and the thickness was 0.250–0.260 inches.

The hardness, friability and release rate of the 650 mg aspirin tablets were determined as described earlier to give the following results:

| Hardness, kg | 7.0–9.0 | |
|---|---|---|
| Friability, % | 0.78 | |
| Release rate | | Cumulative |
| Hour | % | % |
| 1 | 23.1 | 23.1 |
| 2 | 36.1 | 59.2 |
| 3 | 19.7 | 78.9 |
| 4 | 15.5 | 94.4 |
| 5 | 5.2 | 99.6 |

EXAMPLE 6

Controlled release 650 mg aspirin tablets containing 2.7% Methocel E50 and 6.3% Methocel K15M were prepared from the untreated hydroxypropylmethylcelluloses with moisture contents in the range 2–3%.

The 650 mg aspirin tablets were prepared from the following ingredients:

| | Ingredients | grams | mg/tablet |
|---|---|---|---|
| 1 | Aspirin | 650 | 650 |
| 2 | Methocel E50 | 19.5 | 19.5 |
| 3 | Methocel K15M | 45.5 | 45.5 |
| 4 | Lubritab | 7 | 7 |
| 5 | Cab-O-Sil M-5 | 0.5 | 0.5 |

The ingredients were mixed as described in Example 5. The mixture was tableted under a compression pressure of 5000 psi using a 0.281×0.625 inch punch to make 1000 capsule shaped tablets bisected on one side.

The average weight of the tablets was 717 mg and the thickness was 0.250–0.260 inches.

The hardness, friability and release rate of the 650 mg aspirin tablets were determined as described earlier to give the following results:

| Hardness, kg | 7.5–9.0 | |
|---|---|---|
| Friability, % | 0.38 | |
| Release rate | | Cumulative |
| Hour | % | % |
| 1 | 12.7 | 12.7 |
| 2 | 12.7 | 25.4 |
| 3 | 13.3 | 38.7 |
| 4 | 12.5 | 51.2 |
| 5 | 15.4 | 66.6 |
| 6 | 13.4 | 80.0 |
| 7 | 11.8 | 91.8 |
| 8 | 6.3 | 98.1 |

These results demonstrate that effective release rates are obtained from mixtures of hydroxypropylmethylcelluloses when at least one of the polymers has a molecular weight above 50,000.

Examples 7–12 describe the preparation of controlled release 300 mg theophylline tablets.

EXAMPLE 7

Controlled release 300 mg theophylline tablets containing 19.4% Methocel K4M were prepared from untreated Methocel K4M having a moisture content of 2.5%.

The 300 mg theophylline tablets were prepared from the following ingredients:

| | Ingredients | grams | mg/tablet |
|---|---|---|---|
| 1 | Theophylline, anhydrous | 153 | 306 |
| 2 | Methocel K4M | 37.5 | 75 |
| 3 | Cab-O-Sil M-5 | 0.75 | 1.5 |
| 4 | Stearic acid | 1.75 | 3.5 |

Ingredients 1 and 2 were mixed, ingredients 3 and 4 were added and the mixture was then blended for 20 minutes. Tablets were prepared under a compression pressure of 5000 psi using a 0.300×0.545 inch punch to make 500 capsule shaped tablets bisected on one side.

The average weight of the tablets was 392 mg and the thickness was 0.180–0.190 inches.

The hardness, friability and release rates of the 300 mg theophylline tablets were determined in the usual manner to give the following results:

| Hardness, kg | 6.0–8.0 | |
|---|---|---|
| Friability, % | 0.2 | |
| Release rate | | Cumulative |
| Hour | % | % |
| 1 | 19.2 | 19.2 |
| 2 | 12.7 | 31.9 |
| 3 | 12.3 | 44.2 |
| 4 | 11.0 | 55.2 |
| 5 | 11.0 | 66.2 |
| 6 | 11.7 | 77.9 |
| 7 | 10.0 | 87.9 |
| 8 | 5.6 | 93.5 |
| 9 | 6.1 | 99.6 |

EXAMPLE 8

Controlled release 300 mg theophylline tablets containing 19.4% Methocel K15M were prepared from untreated Methocel K15M having a moisture content of 2.0%.

The 300 mg theophylline tablets were prepared from the following ingredients:

| | Ingredients | grams | mg/tablet |
|---|---|---|---|
| 1 | Theophylline, anhydrous | 153 | 306 |
| 2 | Methocel K15M | 37.5 | 75 |
| 3 | Cab-O-Sil M-5 | 0.75 | 1.5 |
| 4 | Stearic acid | 1.75 | 3.5 |

The ingredients were mixed as described in Example 7 and tableted under a compression pressure of 5000 psi using a 0.300×0.545 inch punch to make 500 capsule shaped tablets bisected on one side.

The average weight of the tablets was 388 mg and the thickness was 0.180–0.190 inches.

The hardness, friability and release rates of the 300 mg theophylline tablets were determined in the usual manner to give the following results:

| Hardness, kg | 7.5–8.5 |
|---|---|

-continued

| Friability, % | 0.14 | |
|---|---|---|
| Release rate | | Cumulative |
| Hour | % | % |
| 1 | 17.0 | 17.0 |
| 2 | 12.8 | 29.8 |
| 3 | 9.7 | 39.5 |
| 4 | 8.8 | 48.3 |
| 5 | 8.2 | 56.5 |
| 6 | 8.0 | 64.5 |
| 7 | 7.6 | 72.1 |
| 8 | 7.1 | 79.2 |
| 9 | 7.7 | 86.9 |
| 10 | 5.4 | 92.3 |
| 11 | 2.9 | 95.2 |
| 12 | 3.7 | 98.9 |

EXAMPLE 9

Controlled release 300 mg theophylline tablets containing 17.0% Methocel K4M and 7.3% Methocel K15M were prepared from the untreated polymers, each containing 2.0% moisture.

The 300 mg theophylline tablets were prepared from the following ingredients:

| | Ingredients | grams | mg/tablet |
|---|---|---|---|
| 1 | Theophylline, anhydrous | 306 | 306 |
| 2 | Methocel K4M | 70 | 70 |
| 3 | Methocel K15M | 30 | 30 |
| 4 | Cab-O-Sil M-5 | 1.5 | 1.5 |
| 5 | Stearic acid | 3.5 | 3.5 |

The ingredients were mixed as described in Example 7, adding the premixed Methocel K4M and Methocel K15M to the theophylline and, after mixing, adding the excipient ingredients 4 and 5. Tablets were prepared under 5000 psi pressure using a 0.300×0.545 inch punch to make 1000 capsule shaped tablets having an average weight of 406 mg and a thickness of 0.193-0.203 inches.

The hardness, friability and release rates were determined as described earlier to give the following results:

| Hardness, kg | 4.0-8.0 | |
|---|---|---|
| Friability, % | 0.39 | |
| Release rate | | Cumulative |
| Hour | % | % |
| 1 | 11.4 | 11.4 |
| 2 | 6.8 | 18.2 |
| 3 | 7.5 | 25.7 |
| 4 | 7.3 | 33.0 |
| 5 | 8.4 | 41.4 |
| 6 | 8.9 | 50.3 |
| 7 | 8.7 | 59.0 |
| 8 | 11.7 | 70.7 |
| 9 | 4.4 | 75.1 |
| 10 | 5.9 | 81.0 |
| 11 | 6.3 | 87.3 |
| 12 | 8.4 | 95.7 |
| 13 | 4.4 | 100.1 |

EXAMPLE 10

Controlled release 300 mg theophylline tablets containing 22.4% Methocel K4M were prepared from Methocel K4M which was exposed to 85% humidity for 24 hours and then dried at 120° F. to a moisture content of 4.5%.

The 300 mg theophylline tablets were prepared from the following ingredients:

| | Ingredients | grams | mg/tablet |
|---|---|---|---|
| 1 | Theophylline, anhydrous | 612 | 306 |
| 2 | Methocel K4M | 180 | 90 |
| 3 | Cab-O-Sil M-5 | 3 | 1.5 |
| 4 | Stearic acid | 7 | 3.5 |

The ingredients were mixed as described in Example 7. The resultant mixture was tableted under 5000 psi compression pressure using a 0.300×0.545 inch punch to make 2000 capsule shaped tablets.

The average weight of the tablets was 400 mg and the thickness was 0.185-0.195 inches.

The hardness, friability and release rates of the 300 mg theophylline tablets were determined in the usual manner to give the following results:

| Hardness, kg | 5.0-7.0 | |
|---|---|---|
| Friability, % | 0.3 | |
| Release rate | | Cumulative |
| Hour | % | % |
| 1 | 15.7 | 15.7 |
| 2 | 11.2 | 26.9 |
| 3 | 9.6 | 36.5 |
| 4 | 10.9 | 47.4 |
| 5 | 10.5 | 57.9 |
| 6 | 10.6 | 68.5 |
| 7 | 15.5 | 84.0 |
| 8 | 7.0 | 91.0 |

EXAMPLES 11-12

Tablets with 300 mg theophylline, containing 19.4% of low molecular weight Methocel K35 or Methocel K100, were prepared from untreated Methocel K35 having a number average molecular weight of 19,440 or untreated Methocel K100 having a number average molecular weight of 26,880. The moisture contents of the untreated hydroxypropylmethylcelluloses were in the range of 2-3%.

The 300 mg theophylline tablets were prepared from the following ingredients:

| | Ingredients | grams | mg/tablet |
|---|---|---|---|
| 1 | Theophylline, anhydrous | 153 | 306 |
| 2 | Methocel K35 or K100 | 37.5 | 75 |
| 3 | Cab-O-Sil M-5 | 0.75 | 1.5 |
| 4 | Stearic acid | 1.75 | 3.5 |

The ingredients were mixed as described in Example 7 and tableted under 5000 psi pressure using a 0.300×0.545 inch punch to make 500 capsule shaped tablets bisected on one side.

The average weight of the Methocel K35 tablets was 390 mg while that of the Methocel K100 tablets was 379 mg. The thickness of the former tablets was 0.180-0.190 inches while that of the latter tablets was 0.175-0.185 inches.

The hardness, friability and release rates of the 300 mg theophylline tablets were determined as described earlier to give the following results:

| Example No. | 11 | 12 |
|---|---|---|
| Methocel | K35 | K100 |

| -continued | | | | |
|---|---|---|---|---|
| Hardness, kg | 6.5–8.0 | | 5.4–7.5 | |
| Friability, % | 0.3 | | 0.2 | |
| Release rate | Cumulative | | Cumulative | |
| Hour | % | % | % | % |
| 1 | 85.7 | 85.7 | 92.8 | 92.8 |
| 2 | 15.4 | 101.1 | 2.8 | 95.6 |

These results demonstrate that hydroxypropylmethylcelluloses having a methoxyl content of 19–24 weight-% are ineffective as the sole component of the carrier base when their number average molecular weight is below 50,000.

Examples 13–15 describe the preparation of controlled release 80 mg isosorbide dinitrate tablets.

EXAMPLE 13

Controlled release 80 mg isosorbide dinitrate tablets containing 13.5% Methocel K4M and 5.8% Methocel K15M were prepared from the untreated hydroxypropylmethylcelluloses having moisture contents in the range of 2–3%.

The 80 mg isosorbide dinitrate tablets were prepared from the following ingredients:

| | Ingredients | grams | mg/tablet |
|---|---|---|---|
| 1 | Isosorbide dinitrate (25% in lactose) | 652.8 | 326.4 |
| 2 | Methocel K4M | 112 | 56 |
| 3 | Methocel K15M | 48 | 24 |
| 4 | Stearic acid | 12 | 6 |
| 5 | Silica gel (Syloid 244) | 6 | 3 |

Ingredients 2 and 3 were premixed and added to ingredient 1. After these ingredients were mixed for 15 minutes, a mixture of ingredients 4 and 5, which had passed through a 20 mesh sieve, was added and the resultant mixture was blended for 20 minutes. The mixture was tableted under a pressure of 5000 psi using a 0.300×0.545 inch punch to prepare 2000 capsule shaped bisected tablets.

The average weight of the tablets was 422 mg and the thickness was 0.182–0.192 inches.

The hardness and friability of the 80 mg isosorbide dinitrate tablets were determined as described earlier. The release rates were determined using solutions having the pH indicated in the following table.

| Hardness, kg | 9.0–11.0 | | |
|---|---|---|---|
| Friability, % | 0.15 | | |
| Release rate | | | Cumulative |
| Hour | pH | % | % |
| 1 | 1.5 | 15.8 | 15.8 |
| 2 | 4.5 | 10.6 | 26.4 |
| 3 | 6.9 | 10.5 | 36.9 |
| 4 | 6.9 | 8.1 | 45.0 |
| 5 | 6.9 | 7.4 | 52.4 |
| 6 | 6.9 | 6.6 | 59.0 |
| 7 | 7.2 | 8.0 | 67.0 |
| 8 | 7.2 | 5.7 | 72.7 |
| 9 | 7.2 | 6.7 | 79.4 |
| 10 | 7.2 | 12.9 | 92.3 |
| 11 | 7.2 | 6.2 | 98.5 |

EXAMPLE 14

Controlled release 80 mg isosorbide dinitrate tablets containing 5.8% Methocel K4M and 13.5% Methocel K15M were prepared from the untreated hydroxypropylmethylcelluloses having moisture contents in the range of 2–3%.

The 80 mg isosorbide dinitrate tablets were prepared from the following ingredients:

| | Ingredients | grams | mg/tablet |
|---|---|---|---|
| 1 | Isosorbide dinitrate (25% in lactose) | 652.8 | 326.4 |
| 2 | Methocel K4M | 48 | 24 |
| 3 | Methocel K15M | 112 | 56 |
| 4 | Stearic acid | 12 | 6 |
| 5 | Syloid 244 | 6 | 3 |

The ingredients were mixed as described in Example 13. The mixture was tableted under 6000 psi pressure using a 0.300×0.545 inch punch to make 2000 capsule shaped tablets.

The average weight of the tablets was 414 mg and the thickness was 0.180–0.190 inches.

The hardness, friability and release rates of the 80 mg isosorbide dinitrate tablets were determined as described in Example 13 and gave the following results:

| Hardness, kg | 9.0–12.0 | |
|---|---|---|
| Friability, % | 0.16 | |
| Release rate | | Cumulative |
| Hour | % | % |
| 1 | 11.9 | 11.9 |
| 2 | 7.6 | 19.5 |
| 3 | 7.3 | 26.8 |
| 4 | 7.0 | 33.8 |
| 5 | 10.4 | 44.2 |
| 6 | 9.9 | 54.1 |
| 7 | 7.8 | 61.9 |
| 8 | 7.1 | 69.0 |
| 9 | 6.1 | 75.1 |
| 10 | 4.7 | 79.8 |
| 11 | 3.9 | 83.7 |
| 12 | 3.5 | 87.2 |
| 13 | 10.3 | 97.5 |
| 14 | 3.0 | 100.5 |

EXAMPLE 15

Controlled release 80 mg isosorbide dinitrate tablets containing 9.6% Methocel K4M and 9.6% Methocel E4M were prepared from the untreated Methocel K4M containing 2.8% moisture and the untreated Methocel E4M containing 2.5% moisture.

The 80 mg isosorbide dinitrate tablets were prepared from the following ingredients:

| | Ingredients | grams | mg/tablet |
|---|---|---|---|
| 1 | Isosorbide dinitrate (25% in lactose) | 326.4 | 326.4 |
| 2 | Methocel K4M | 40 | 40 |
| 3 | Methocel E4M | 40 | 40 |
| 4 | Stearic acid | 6 | 6 |
| 5 | Syloid 244 | 3 | 3 |

The ingredients were mixed as described in Example 13. The mixture was tableted under 6000 psi pressure to make 1000 capsule shaped tablets, using a 0.300×0.545 inch punch.

The average weight of the tablets was 418 mg and the thickness was 0.189–0.195 inches.

The hardness, friability and release rates of the 80 mg isosorbide dinitrate tablets were determined as described in Example 13 and gave the following results:

| Hardness, kg | 6.5-8.5 | |
|---|---|---|
| Friability, % | 0.2 | |
| Release rate | | Cumulative |
| Hour | % | % |
| 1 | 40.7 | 40.7 |
| 2 | 11.2 | 51.9 |
| 3 | 7.2 | 59.1 |
| 4 | 7.3 | 66.4 |
| 5 | 6.7 | 73.1 |
| 6 | 5.7 | 78.8 |
| 7 | 7.9 | 86.7 |
| 8 | 3.5 | 90.2 |
| 9 | 6.0 | 96.2 |

Examples 16-19 describe the preparation of controlled release 300 mg lithium carbonate tablets.

EXAMPLE 16

Controlled release 300 mg lithium carbonate tablets containing 24.8% Methocel K15M were prepared from Methocel K15M which had been exposed to 85% humidity for 24 hours and then dried in a forced air oven at 120° F. until the moisture content was 5.0%.

The 300 mg lithium carbonate tablets were prepared from the following ingredients:

| | Ingredients | grams | mg/tablet |
|---|---|---|---|
| 1 | Lithium carbonate | 300 | 300 |
| 2 | Methocel K15M | 100 | 100 |
| 3 | Cherry flavor | 1.2 | 1.2 |
| 4 | Magnesium stearate | 1.6 | 1.6 |

Ingredients 1 and 2 were mixed, ingredient 3 was added and mixed in, followed by the addition of ingredient 4. After mixing for 20 minutes, the mixture was tableted under 5000 psi compression pressure using a 13/32 inch tool to prepare 1000 round, flat faced beveled tablets bisected on one side.

The average weight of the tablets was 395 mg and the thickness was 0.120-0.140 inches.

The hardness and friability of the 300 mg lithium carbonate tablets were determined as described earlier. The release rates were determined using solutions having the pH indicated in the following table:

| Hardness, kg | | 6.0-9.0 | | | | | |
|---|---|---|---|---|---|---|---|
| Friability, % | | 0.29 | | | | | |
| Release rate | | | Cumulative | | | | Cumulative |
| Hour | pH | % | % | Hour | pH | % | % |
| 1 | 1.2 | 14.2 | 14.2 | 13 | 7.5 | 3.6 | 72.5 |
| 2 | 2.5 | 11.3 | 25.5 | 14 | 7.5 | 3.9 | 76.4 |
| 3 | 4.5 | 5.6 | 31.1 | 15 | 7.5 | 3.5 | 79.9 |
| 4 | 7.0 | 5.4 | 36.5 | 16 | 7.5 | 3.3 | 83.2 |
| 5 | 7.0 | 5.3 | 41.8 | 17 | 7.5 | 4.1 | 87.3 |
| 6 | 7.5 | 3.9 | 45.7 | 18 | 7.5 | 2.7 | 90.0 |
| 7 | 7.5 | 4.0 | 49.7 | 19 | 7.5 | 2.5 | 92.5 |
| 8 | 7.5 | 3.3 | 53.0 | 20 | 7.5 | 2.2 | 94.7 |
| 9 | 7.5 | 4.2 | 57.2 | 21 | 7.5 | 2.1 | 96.8 |
| 10 | 7.5 | 4.0 | 61.2 | 22 | 7.5 | 1.7 | 98.5 |
| 11 | 7.5 | 3.7 | 64.9 | 23 | 7.5 | 1.6 | 100.1 |
| 12 | 7.5 | 4.0 | 68.9 | 24 | 7.5 | 1.2 | 101.3 |

EXAMPLE 17

Controlled release 300 mg lithium carbonate tablets containing 14.2% Methocel K15M were prepared using Methocel K15M which had been humidified in an 85% humidity chamber and then dried at 120° F. to a moisture content of 5.0%.

The 300 mg lithium carbonate tablets were prepared from the following ingredients:

| | Ingredients | grams | mg/tablet |
|---|---|---|---|
| 1 | Lithium carbonate | 300 | 300 |
| 2 | Methocel K15M | 50 | 50 |
| 3 | Cherry flavor | 1.2 | 1.2 |
| 4 | Magnesium stearate | 1.6 | 1.6 |

The ingredients were mixed as described in Example 16 and the mixture was tableted under a pressure of 5000 psi using a 11/32 inch tool to prepare 1000 round, flat beveled tablets.

The average weight of the tablets was 354 mg and the thickness was 0.155-0.165 inches.

The hardness, friability and release rates of the 300 mg lithium carbonate tablets were determined as described in Example 16 and gave the following results:

| Hardness, kg | 3.8-4.0 | |
|---|---|---|
| Friability, % | 0.25 | |
| Release rate | | Cumulative |
| Hour | % | % |
| 1 | 23.3 | 23.3 |
| 2 | 11.0 | 34.3 |
| 3 | 10.5 | 44.8 |
| 4 | 8.5 | 53.3 |
| 5 | 8.3 | 61.6 |
| 6 | 6.8 | 68.4 |
| 7 | 7.6 | 76.0 |
| 8 | 5.4 | 81.4 |
| 9 | 5.3 | 86.7 |
| 10 | 4.3 | 91.0 |
| 11 | 3.2 | 94.2 |
| 12 | 4.7 | 98.9 |

EXAMPLE 18

Controlled release 300 mg lithium carbonate tablets containing 19.9% Methocel K15M were prepared using untreated Methocel K15M having a moisture content of 1.5%.

The 300 mg lithium carbonate tablets were prepared from the following ingredients:

| | Ingredients | grams | mg/tablet |
|---|---|---|---|
| 1 | Lithium carbonate | 300 | 300 |
| 2 | Methocel K15M | 75 | 75 |
| 3 | Magnesium stearate | 0.8 | 0.8 |
| 4 | Cab-O-Sil M-5 | 1.0 | 1.0 |

The ingredients were mixed as described in Example 16. An 11/32 inch flat faced bevel tool was used to prepare 1000 white round tablets under 5000 psi pressure. The average weight of the tablets was 380 mg, the thickness was 0.170-0.180 inches and the hardness was 6.0-6.5 kg.

EXAMPLE 19

Controlled release 300 mg lithium carbonate tablets containing 19.9% Methocel K4M were prepared using untreated Methocel K4M having a moisture content of 2.0%.

The tablets were prepared from the following ingredients:

| | Ingredients | grams | mg/tablet |
|---|---|---|---|
| 1 | Lithium carbonate | 300 | 300 |
| 2 | Methocel K4M | 75 | 75 |
| 3 | Magnesium stearate | 0.8 | 0.8 |
| 4 | Cab-O-Sil M-5 | 1.0 | 1.0 |

The ingredients were mixed as described in Example 16 and the mixture was compressed using an 11/32 inch flat faced bevel tool to prepare 1000 white round tablets. The average weight of the 300 mg lithium carbonate tablets was 376 mg, the thickness was 0.165–0.170 inches and the hardness was 6.0 kg.

Examples 20–22 describe the preparation of controlled release nitroglycerin tablets.

EXAMPLES 20–21

Controlled release 6.5 mg nitroglycerin tablets containing 24% Methocel K4M were prepared from untreated Methocel K4M having a moisture content of 2.5% as well as from Methocel K4M which had been humidified and then dried at 120° F. to a moisture content of 5.0%, as described earlier.

The 6.5 mg nitroglycerin tablets were prepared from the following ingredients:

| | Ingredients | Untreated Methocel K4M grams | Treated Methocel K4M grams | mg/tablet |
|---|---|---|---|---|
| 1 | Nitroglycerin (10% in lactose) | 130 | 195 | 65 |
| 2 | Lactose, anhydrous | 80 | 120 | 40 |
| 3 | Methocel K4M | 70 | 105 | 35 |
| 4 | FDC Red No. 3 | 0.6 | 0.9 | 0.3 |
| 5 | Stearic acid | 6 | 9 | 3 |
| 6 | Syloid 244 | 2 | 3 | 1 |
| 7 | Cab-O-Sil M-5 | 2 | — | 1 |

Ingredients 1, 2, 3 and 4 were mixed together and passed through a 20 mesh sieve. Ingredients 5 and 6, and 7 when used, were mixed, passed through a 20 mesh sieve and then mixed with the mixture of the other ingredients. After 20 minutes of blending, the mixture was compressed using a 9/32 inch tool to prepare 2000 pink, round and concave shaped tablets bisected on one side from the untreated Methocel K4M and 3000 similar tablets from the treated Methocel K4M.

The tablets from the untreated Methocel K4M had an average weight of 150 mg and a thickness of 0.135–0.145 inches. The tablets from the treated Methocel K4M had an average weight of 148 mg and a thickness of 0.130–0.140 inches.

The hardness and friability of the 6.5 mg nitroglycerin tablets were determined in the usual manner. The release rates were determined using solutions having the same pH as used with the isosorbide dinitrate tablets in Example 13. The results were as follows:

| | Example No. | | | |
|---|---|---|---|---|
| | 20 | | 21 | |
| Methocel K4M | Untreated | | Treated | |
| Hardness, kg | 3.0–4.5 | | 3.0–3.5 | |
| Friability, % | 0.3 | | 0.3 | |
| Release rate Hour | % | Cumulative % | % | Cumulative % |
| 1 | 26.6 | 26.6 | 23.7 | 23.7 |
| 2 | 17.5 | 44.1 | 13.8 | 37.5 |
| 3 | 14.2 | 58.3 | 13.3 | 50.8 |
| 4 | 11.6 | 69.9 | 18.2 | 69.0 |
| 5 | 10.0 | 79.9 | 16.7 | 85.7 |
| 6 | 7.7 | 87.6 | 12.4 | 98.1 |
| 7 | 5.4 | 93.0 | | |
| 8 | 3.8 | 96.8 | | |

EXAMPLE 22

Controlled release 5.5 mg nitroglycerin buccal tablets containing 11.1% Methocel K4M were prepared from untreated Methocel K4M having a moisture content of 1.6%.

The 5.5 mg nitroglycerin buccal tablets were prepared from the following ingredients:

| | Ingredients | grams | mg/tablet |
|---|---|---|---|
| 1 | Nitroglycerin (10% in lactose) | 275 | 5.5 |
| 2 | Lactose, anhydrous | 237.5 | 47.5 |
| 3 | Methocel K4M | 35 | 7 |
| 4 | Stearic acid | 5 | 1 |
| 5 | Syloid 244 | 5 | 1 |
| 6 | Cab-O-Sil M-5 | 5 | 1 |

Ingredient 1 was passed through a 20 mesh sieve. Ingredient 2 was added and mixed, followed by ingredient 3. A mixture of ingredients 4, 5 and 6 was added and mixed. The mixture was compressed using a ¼ inch concave tool to prepare 5000 white, round buccal tablets.

The average weight of the tablets was 120 mg, the thickness was 0.130–0.140 inches.

EXAMPLE 23

This example describes the preparation of 5.5 mg controlled release phenylpropanolamine base buccal tablets containing 25.8% Methocel K4M wherein the latter was subjected to humidification in an 85% relative humidity chamber for 24 hours and then dried at 120° F. to reduce the moisture content to 4.5%.

The 5.5 mg phenylpropanolamine tablets were prepared from the following ingredients:

| | Ingredients | grams | mg/tablet |
|---|---|---|---|
| 1 | Phenylpropanolamine base | 11 | 5.5 |
| 2 | Lactose, anhydrous | 100 | 50 |
| 3 | Methocel K4M | 40 | 20 |
| 4 | Spearmint flavor | 1 | 0.5 |
| 5 | Peppermint flavor | 1 | 0.5 |
| 6 | Stearic acid | 2 | 1 |

Ingredients 1, 2, 4 and 5 were mixed. Ingredient 3 was then added and mixed for 10 minutes. Ingredient 6 was added and the mixture was blended for 20 minutes. The mixture was tableted under 5000 psi pressure using a ¼ inch concave punch to produce 2000 white round buccal tablets.

The average weight of the tablets was 78 mg and the thickness was 0.105–0.110 inches. The hardness, friability and release rates of the buccal tablets were determined as described in Example 22 and gave the following results:

| Hardness, Kg | 4.5–6.0 | |
|---|---|---|
| Friability, % | 0.8 | |
| Release rate | Minutes | Cumulative % |
| | 15 | 27.6 |
| | 30 | 39.0 |
| | 45 | 50.0 |
| | 60 | 60.2 |
| | 90 | 73.0 |
| | 120 | 83.2 |

EXAMPLE 24

This example describes the preparation of controlled release 600 mg potassium chloride lozenges containing 24.8% untreated Methocel K15M.

The 600 mg lozenges were prepared from the following ingredients:

| | Ingredients | grams | mg/tablet |
|---|---|---|---|
| 1 | Potassium chloride | 600 | 600 |
| 2 | Methocel K15M | 200 | 200 |
| 3 | Stearic acid | 8 | 8 |

Ingredient 1 was passed through a 40 mesh sieve. Ingredient 2 was added and mixed with ingredient 1. Ingredient 3 was passed through a 40 mesh sieve and then mixed with ingredients 1 and 2 for 20 minutes.

The mixture was compressed under 5000 psi using a 7/16 inch deep concave punch to prepare 1000 round mottled white lozenges.

The average weight of the lozenges was 810 mg and the thickness was 0.255–0.265 inches.

The hardness, friability and release rates of the lozenges were determined as described in Example 22 and gave the following results:

| Hardness, kg | 6.0–8.5 | |
|---|---|---|
| Friability, % | 0.13 | |
| Release rate | Hour | Cumulative % |
| | 1 | 71.2 |
| | 2 | 87.4 |
| | 3 | 99.3 |

Examples 25 to 27 disclose compositions containing anti-inflammatory drugs such as ibuprofen, flurbiprofen, diclofenac, indomethacin and naproxen.

EXAMPLE 25

Controlled release 700 mg ibuprofen tablets containing 9.5% Methocel K4M and 9.0% Methocel K15M were prepared from the untreated hydroxypropylmethylcelluloses having moisture contents in the range of 2.0–3.0%.

A tablet having the following composition was prepared in the usual manner:

| | Ingredients | mg/table |
|---|---|---|
| 1 | Ibuprofen | 700 |
| 2 | PVP | 20 |
| 3 | Methocel K4M | 85 |
| 4 | Methocel K15M | 80 |
| 4 | Syloid | 5 |
| 6 | Stearic Acid | 1 |

The tablets were compressed using 0.750"×0.300" capsule-shaped bisected punches at a compressional force of about 4000 lbs/sq.in. to obtain a tablet of average weight of 893 mg and a hardness of 8 to 10 kg.

EXAMPLE 26

Controlled release 200 mg flurbiprofen tablets containing 12.4% Methocel K4M and 10.2% Methocel K15M were prepared from the untreated hydroxypropylmethylcelluloses having moisture contents in the range of 2.0–3.0%.

A tablet having the following composition was prepared in the usual manner:

| | Ingredients | mg/tablet |
|---|---|---|
| 1 | Flurbiprofen | 200 |
| 2 | Methocel K4M | 33 |
| 3 | Methocel K15M | 27 |
| 4 | Stearic Acid | 5 |
| 5 | Cab-O-Sil M-5 | 1 |

Tablets were compressed using 0.281"×0.625" capsule-shaped bisected punches at a compressional pressure of 4000 to 6000 lbs/sq.in. to obtain a tablet of average weight of 270 mg and a hardness of 6 to 8 kg.

EXAMPLE 27

Controlled release 100 mg diclofenac tablets containing 8.5% Methocel K4M and 12.8% Methocel K15M were prepared from the untreated hydroxypropylmethylcelluloses having moisture contents in the range of 2.0–3.0%.

A tablet having the following composition was prepared in the usual manner:

| | Ingredients | mg/tablet |
|---|---|---|
| 1 | Diclofenac sodium | 100 |
| 2 | P.V.P. | 5 |
| 3 | Methocel K4M | 12 |
| 4 | Methocel K15M | 18 |
| 5 | Stearic Acid | 5 |
| 6 | Cab-O-Sil M-5 | 1 |

Tablets were compressed using 9/32" standard concave round punches at a compressional pressure of 4000 to 6000 lbs/sq.in. to give a tablet weight of 144 mg and a hardness of 6 to 8 kg.

The foregoing is exemplary and illustrative of compositions and products responding to the present invention, but it is to be understood that they are not limitative since many active medicaments of various types can be employed in the new long-lasting carrier so long as they are absorbable into blood or tissue from the general intestinal tract and other bodily surfaces and areas. The medicaments shown in our co-pending application Ser. No. 332,348 filed Dec. 18, 1981 may be used in the practice of the present invention and are incorporated herein by reference. The invention is also intended to cover other dosage forms or forms for application of sustained release ingredients such as vaginal and rectal suppositories. The lozenges and tablets particularly act on oral, oropharyngeal, pharyngeal and intestinal regions. The total dosage is governed by usual medical considerations or physicians' directions and when sufficiently large doses of active medicament are incorporated in the unit dosage form, systemic as well as local action is obtained to overcome or control the pathological condition or disorder being treated.

What is claimed is:

1. A carrier base material combined with a therapeutically active medicament and shaped and compressed to a solid unit dosage form having a regular and prolonged release pattern upon administration, the carrier base material being one or more hydroxypropylmethylcelluloses or a mixture of one or more hydroxypropylmethylcelluloses and up to 30% by weight of the mixture of methyl cellulose, sodium carboxymethylcellulose and/or other cellulose ether, and wherein at least one of the hydroxypropylmethylcelluloses has a methoxy content of 16-24 weight-%, a hydroxypropoxyl content of 4-32 weight-% and a number average molecular weight of at least 50,000 and wherein the carrier base material constitutes less than about one third of the weight of the solid unit dosage form.

2. A composition according to claim 1 in which the carrier base material consists of a mixture of one or more hydroxypropylmethylcelluloses and 0-30% sodium carboxymethylcellulose.

3. A composition according to claim 1 in which the carrier base material consists of a mixture of one or more hydroxypropylmethylcelluloses and 0-30% of methylcellulose or other cellulose ether.

4. A composition according to claim 1 in which the active medicament is a moisture sensitive material.

5. A composition according to claim 4 in which the moisture sensitive medicament is selected from but not limited to aspirin, theophylline, phenacetin, procainamide, nikethamide, polymixin, barbiturates, idoxuridine, hydantoins, angiotensinamide, nitroglycerin, isosorbide dinitrate, benzocaine, scopolamine, meperidine, codeine, morphine, streptomycin, ascorbic acid, sulfonamide drugs, tolbutamide, chlorpheniramine, brompheniramine, phenylephrine, diphenhydramine, penicillins, tropine alkaloids, diethylcarbamazine, dihydroergotamine, caffeine, dexamethasone, and pharmaceutically acceptable salts of any of the above, alkaloid salts and adrenocortical steroid esters.

6. A composition according to claim 1 in which the active medicament is lithium carbonate.

7. A composition according to claim 1 in which the active medicament is phenylpropanolamine.

8. A composition according to claim 1 in which the active medicament is potassium chloride.

9. A composition according to claim 1 in which the active medicament is an anti-inflammatory drug selected from and not limited to ibuprofen, flurbiprofen, diclofenac, indomethacin and naproxen.

10. A method for the preparation of a therapeutically active solid unit dosage form having a regular and prolonged release pattern upon administration, consisting of compressing and shaping a mixture of a therapeutically active medicament and a carrier base material consisting of one or more hydroxypropylmethylcelluloses or a mixture of one or more hydroxypropylmethylcelluloses and up to 30% by weight of the mixture of methylcellulose, sodium carboxymethylcellulose or other cellulose ether, and wherein at least one of the hydroxypropylmethylcelluloses has a methoxyl content of 16-24 weight-%, a hydroxypropoxyl content of 4-32 weight-% and a number average molecular weight of at least 50,000, and wherein the carrier base material constitutes less than about one third of the weight of the solid unit dosage form.

* * * * *

REEXAMINATION CERTIFICATE (405th)

United States Patent [19]

Schor et al.

[11] B1 4,389,393

[45] Certificate Issued    Oct. 22, 1985

[54] SUSTAINED RELEASE THERAPEUTIC COMPOSITIONS BASED ON HIGH MOLECULAR WEIGHT HYDROXYPROPYLMETHYLCELLULOSE

[75] Inventors: Joseph M. Schor, Locust Valley; Ashok Nigalaye, Jackson Heights, both of N.Y.; Norman G. Gaylord, New Providence, N.J.

[73] Assignee: Forest Laboratories, Inc., New York, N.Y.

Reexamination Reqs:st:
No. 90/000,713, Jan. 23, 1985
No. 90/000,461, Oct. 18, 1983

Reexamination Certificate for:
Patent No.:    4,389,393
Issued:        Jun. 21, 1983
Appl. No.:     362,104
Filed:         Mar. 26, 1982

[51] Int. Cl.⁴ ............................................. A61K 9/50
[52] U.S. Cl. ....................................... 424/19; 424/22; 424/35; 514/164; 514/781; 514/57
[58] Field of Search .................................. 424/19–22, 424/35; 514/57

[56]         References Cited

U.S. PATENT DOCUMENTS

| | | | |
|---|---|---|---|
| 3,065,143 | 11/1962 | Christenson et al. | 167/82 |
| 4,167,558 | 9/1979 | Sheth et al. | 424/22 |
| 4,226,849 | 10/1980 | Schor | 424/19 |
| 4,357,469 | 11/1982 | Schor | 536/91 |
| 4,870,790 | 3/1975 | Lowey et al. | 424/19 |

OTHER PUBLICATIONS

Chemical Abstracts, 68:89862g (1968).
Dissertation Abstracts, B, 28(6) pp. 2363–2364 (1967).
"Methocel" The Dow Chemical Company, pp. 1–6 (1962).
"Methocel Product Information–Viscosity of Aqueous Fluids", The Dow Chemical Company, (1966).
Handbook on Methocel Cellulose Ether Products, The Dow Chemical Company, (1974).
Handbook on Methocel Cellulose Ether Products, The Dow Chemical Company, pp. 1.1–1.2; 3.1–3.3; 6.3–6.4.
"Metolose" Shinetsu Chemical, (1975).
Encyclopedia of Polymer Science and Technology; vol. 3, p. 504 (1965).
Lapidus et al., "Drug Release from Compressed Hydrophilic Matrices", J. Pharm. Sci., 57, pp. 1292–1301 (1968).
Lapidus, "Drug Release from Compressed Hydrophilic Matrices", Doctoral Dissertation, Rutgers-The State University, 1967, (University Microfilms, No. 67-14,728).
Huber et al., "Utilization Gums for the Control of Drug Release from Tablet Formulations I.", J. Pharm Sci., 55, pp. 974–976 (1976).
Salomon et al., "Importance de la technologie et de la formulation pour le mechanisme de liberation du chlorure de potassium contenu dans des matrices hydrophiles", Pharm. Acta (Helv), 54, pp. 82–85 (1978).
Hoffman-LaRoche, Publication No. RCD 2986R/0880, (Aug. 1980).

*Primary Examiner*—Johnnie R. Brown

[57]           ABSTRACT

A carrier base material combined with a therapeutically active medicament and shaped and compressed to a solid unit dosage form having a regular and prolonged release pattern upon administration, the carrier base material being one or more hydroxypropylmethylcelluloses or a mixture of one or more hydroxypropylmethylcelluloses and up to 30% by weight of the mixture of methylcellulose, sodium carboxymethylcellulose and/or other cellulose ether, and wherein at least one of the hydroxypropylmethylcelluloses has a methoxy content of 16–24 weight-%, a hydroxypropoxyl content of 4–32 weight-% and a number average molecular weight of at least 50,000 and wherein the carrier base material constitutes less than about one third of the weight of the solid unit dosage form.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-10 are cancelled.

New claims 11-22 are added and determined to be patentable.

*11. A carrier base material combined with a therapeutically active medicament and shaped and compressed to a solid unit dosage form having a regular and prolonged release pattern upon administration, the carrier base material comprising one or more hydroxypropylmethylcelluloses or a mixture of one or more hydroxypropylmethylcelluloses and up to 30% by weight of the mixture of methyl cellulose, sodium carboxymethylcellulose and/or other cellulose ether, and wherein at least one of the hydroxypropylmethylcelluloses has a methoxy content of 16-24 weight-%, a hydroxypropoxyl content of 4-32 weight-%, and a number average molecular weight of at least 50,000 and wherein the carrier base material constitutes 25.8 weight-% or less of the solid unit dosage form and at least four hours are required for release of 94.4% of the medicament from the dosage form following administration.*

*12. A carrier base material combined with a therapeutically active medicament and shaped and compressed to a solid unit dosage form having a regular and prolonged release pattern upon administration, the carrier base material comprising one or more hydroxypropylmethylcelluloses or a mixture of one or more hydroxypropylmethylcelluloses and up to 30% by weight of the mixture of methyl cellulose, sodium carboxymethylcellulose and/or other cellulose ether, and wherein at least one of the hydroxypropylmethylcelluloses has a methoxy content of 16-24 weight-%, a hydroxypropoxyl content of 4-32 weight-%, and a number average molecular weight of at least 50,000 and wherein the carrier base material constitutes 14.2 weight-% or less of the solid unit dosage form and at least four hours are required for release of 94.4% of the medicament from the dosage form following administration.*

*13. A carrier base material combined with a therapeutically active medicament and shaped and compressed to a solid unit dosage form having a regular and prolonged release pattern upon administration, the carrier base material comprising one or more hydroxypropylmethylcelluloses or a mixture of one or more hydroxypropylmethylcelluloses and up to 30% by weight of the mixture of methyl cellulose, sodium carboxymethylcellulose and/or other cellulose ether, and wherein at least one of the hydroxypropylmethylcelluloses has a methoxy content of 16-24 weight-%, a hydroxypropoxyl content of 4-32 weight-%, and a number average molecular weight of at least 50,000 and wherein the carrier base material constitutes 25.8 weight-% or less of the solid unit dosage form and at least six hours are required for release of 98.1% of the medicament from the dosage form following administration.*

*14. A carrier base material combined with a therapeutically active medicament and shaped and compressed to a solid unit dosage form having a regular and prolonged release pattern upon administration, the carrier base material comprising one or more hydroxypropylmethylcelluloses or a mixture of one or more hydroxypropylmethylcelluloses and up to 30% by weight of the mixture of methyl cellulose, sodium carboxymethylcellulose and/or other cellulose ether, and wherein at least one of the hydroxypropylmethylcelluloses has a methoxy content of 16-24 weight-%, a hydroxypropoxyl content of 4-32 weight-%, and a number average molecular weight of at least 50,000 and wherein the carrier base material constitutes 14.2 weight-% or less of the solid unit dosage form and at least six hours are required for release of 98.1% of the medicament from the dosage form following administration.*

*15. The composition according to any of claims 11 to 14 wherein at least 5 weight-% of the dosage form is one or more hydroxypropylmethylcelluloses having a methoxy content of 16-24 weight-%, a hydroxypropoxyl content of 4-32 weight-%, and a number average molecular weight of at least 50,000.*

*16. A composition according to any of claims 11 to 14 in which the carrier base material consists of a mixture of one or more hydroxypropylmethylcelluloses and 0-30% sodium carboxymethylcellulose.*

*17. A composition according to any of claims 11 to 14 in which the carrier base material consists of a mixture of one or more hydroxypropylmethylcelluloses and 0-30% of methylcellulose or other cellulose ether.*

*18. A composition according to any of claims 11 to 14 in which the active medicament is a moisture sensitive material.*

*19. A composition according to any of claims 11 to 14 in which the medicament is selected from the group consisting of aspirin, theophylline, phenacetin, procainamide, nikethamide, polymixin, barbiturates, idoxuridine, hydantoins, angiotensinamide, nitroglycerin, isosorbide dinitrate, benzocaine, scopolamine, meperidine, codeine, morphine, streptomycin, ascorbic acid, sulfonamide drugs, tolbutamide, chlorpheniramine, brompheniramine, phenylephrine, diphenhydramine, penicillins, tropine alkaloids, diethylcarbamazine, dihydroergotamine, caffeine, dexamethasone, and pharmaceutically acceptable salts of any of the above, alkaloid salts, and adrenocortical steroid esters.*

*20. A composition according to any of claims 11 to 14 in which the active medicament is lithium carbonate.*

*21. A composition according to any of claims 11 to 14 in which the active medicament is phenylpropanolamine.*

*22. A composition according to any of claims 11 to 14 in which the active medicament is an anti-inflammatory drug selected from ibuprofen, flurbiprofen, diclofenac, indomethacin, and naproxen.*

* * * * *